(12) United States Patent
Khanna

(10) Patent No.: US 8,123,789 B2
(45) Date of Patent: Feb. 28, 2012

(54) CENTRAL NERVOUS SYSTEM COOLING CATHETER

(76) Inventor: Rohit Khanna, Daytona Beach, FL (US)

( * ) Notice: Subject to any disclaimer, the term of this patent is extended or adjusted under 35 U.S.C. 154(b) by 1548 days.

(21) Appl. No.: 11/418,849

(22) Filed: May 5, 2006

(65) Prior Publication Data

US 2007/0005121 A1    Jan. 4, 2007

Related U.S. Application Data

(63) Continuation of application No. 10/136,003, filed on Dec. 20, 2002, now Pat. No. 6,699,269.

(51) Int. Cl.
*A61F 7/00* (2006.01)

(52) U.S. Cl. .............. 607/105; 607/104; 606/23

(58) Field of Classification Search ............ 604/512, 604/113; 607/104–106; 606/108
See application file for complete search history.

(56) References Cited

U.S. PATENT DOCUMENTS

| | | | |
|---|---|---|---|
| 3,556,079 A | 1/1971 | Omizo | |
| 4,210,029 A | 7/1980 | Porter et al. | |
| 4,431,006 A | 2/1984 | Trimmer et al. | |
| 4,740,047 A | 4/1988 | Abe et al. | |
| 4,887,606 A | 12/1989 | Yock et al. | |
| 4,904,237 A | 2/1990 | Janese | |
| 4,911,170 A | 3/1990 | Thomas, III et al. | |
| 5,002,059 A | 3/1991 | Crowley et al. | |
| 5,022,399 A | 6/1991 | Beigeleisen | |
| 5,163,421 A | 11/1992 | Bernstein et al. | |
| 5,197,946 A | 3/1993 | Tachibana | |
| 5,209,721 A | 5/1993 | Wilk | |
| 5,269,291 A | 12/1993 | Carter | |
| 5,269,297 A | 12/1993 | Weng | |
| 5,315,998 A | 5/1994 | Tachibana et al. | |
| 5,318,014 A | 6/1994 | Carter | |
| 5,324,255 A | 6/1994 | Passafaro et al. | |
| 5,345,940 A | 9/1994 | Seward et al. | |
| 5,362,309 A | 11/1994 | Carter | |
| 5,428,699 A | 6/1995 | Pon | |
| 5,699,805 A | 12/1997 | Seward et al. | |
| 5,735,811 A | 4/1998 | Brisken | |
| 5,902,268 A * | 5/1999 | Saab | 604/96.01 |
| 6,001,069 A | 12/1999 | Tachibana et al. | |
| 6,024,718 A | 2/2000 | Chen et al. | |
| 6,264,679 B1 * | 7/2001 | Keller et al. | 607/105 |
| 6,338,727 B1 | 1/2002 | Noda et al. | |
| 6,379,331 B2 | 4/2002 | Barbut et al. | |
| 6,428,531 B1 | 8/2002 | Visuri et al. | |
| 6,506,189 B1 | 1/2003 | Rittman et al. | |
| 6,527,763 B2 | 3/2003 | Esch et al. | |
| 6,527,798 B2 | 3/2003 | Ginsburg et al. | |
| 6,620,188 B1 * | 9/2003 | Ginsburg et al. | 607/106 |
| 6,623,490 B1 * | 9/2003 | Crane et al. | 606/108 |
| 6,699,269 B2 | 3/2004 | Khanna | |
| 6,723,063 B1 | 4/2004 | Zhang et al. | |
| 6,723,064 B2 | 4/2004 | Babaev | |
| 7,144,418 B1 * | 12/2006 | Lennox | 607/105 |
| 2002/0022823 A1 * | 2/2002 | Luo et al. | 604/512 |
| 2002/0082556 A1 * | 6/2002 | Cioanta et al. | 604/113 |

* cited by examiner

*Primary Examiner* — Roy Gibson

(57) ABSTRACT

The invention provides a method and apparatus for performing selective hypothermia to the brain and spinal cord for injury protection without the need for systemic cooling. A flexible catheter is inserted into the cerebral lateral ventricle or spinal subdural space. The catheter has lumens with a heat transfer element. The lumens of the catheter circulate a coolant and communicate at the distal heat transfer element for transfer of heat from the cerebrospinal fluid. Furthermore a method of maintaining catheter patency and providing blood clot hemolysis and drainage is also provided through the use of ultrasonic and/or laser energy delivered through the catheter.

25 Claims, 21 Drawing Sheets

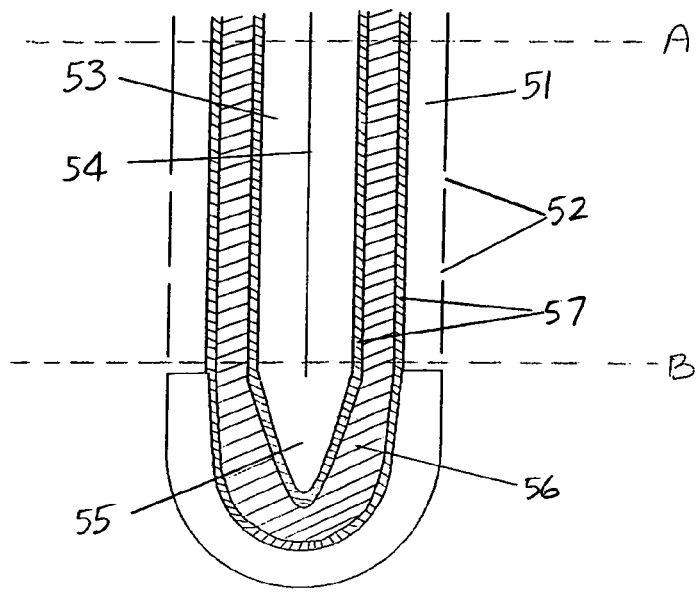
FIG. 25
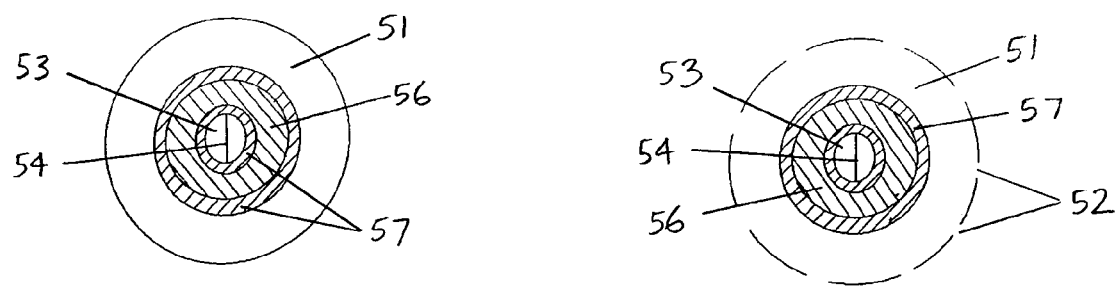
FIG. 26
FIG. 27

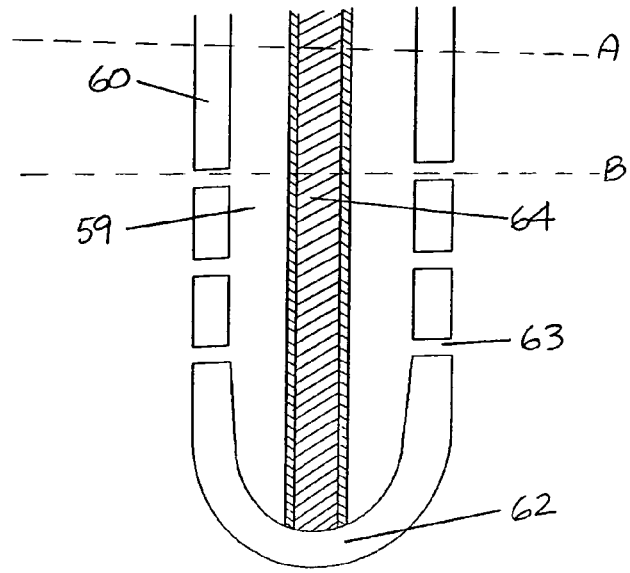
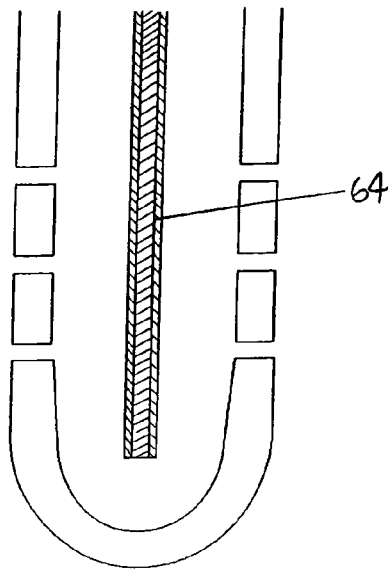
FIG. 28            FIG. 29
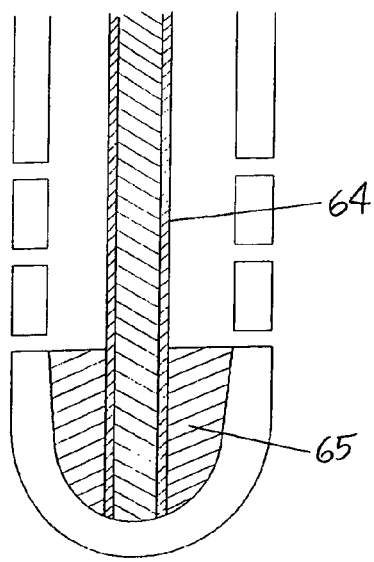
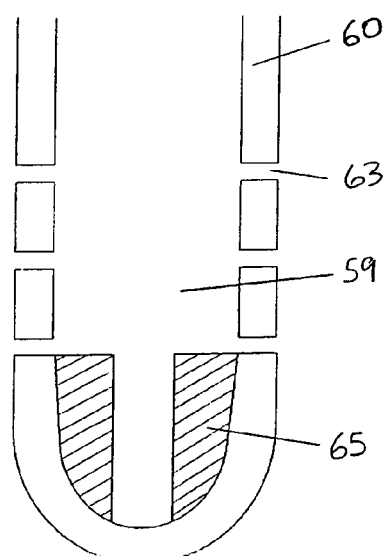
FIG. 30            FIG. 31

CENTRAL NERVOUS SYSTEM COOLING CATHETER

This application is a continuation of U.S. application Ser. No. 10/136,003 filed Dec. 20, 2002, titled "Selective brain and spinal cord hypothermia method and apparatus," now U.S. Pat. No. 6,699,269.

BACKGROUND OF THE INVENTION

The current invention relates to regulation of the temperature in the brain and spinal cord. The invention describes a method and apparatus for altering the temperature of the brain surface and/or the cerebrospinal fluid in the ventricles of the brain and surrounding the spinal cord.

Hypothermia has been shown to provide cerebral and spinal cord injury protection from either trauma, ischemia, or hypoxia. Ischemia may occur from cardiac arrest, cardiac failure, stroke, head or spinal cord injury, aneurysm surgery, cardiac surgery, and aortic or carotid surgery. Hypothermia is also effective in reducing increased intracranial pressure from cerebral swelling. The mechanisms involved in hypothermic cerebral protection are several-fold and include 1) reduction in cerebral glucose and oxygen metabolism and decreasing lactate content following injury, 2) preventing disruption of the blood brain barrier and consequently reducing cerebral edema, 3) reduction of endogenously toxic neurotransmitters like glutamate, glycine, aspartate, acetylcholine, and norepinephrine into the brain after injury, 4) inhibit excessive calcium entry and intracellular calcium overload into neurons, 5) protecting membrane structural proteins like microtubule-associated protein-2, and 6) preventing diffuse axonal injury following brain trauma.

In general, the human brain and spinal cord are maintained at a constant temperature of approximately 37 to 38 degrees celsius. Hypothermia is considered mild when the body temperature is 33 to 35 degrees celsius, moderate between the temperatures of 28 to 32 degrees, and severe in the temperature range of 24 to 28 degrees celsius. Most studies in humans have involved mild to moderate systemic hypothermia mainly because of the significant side effects that occur from induced systemic hypothermia. These include infection, cardiac arrhythmias, coagulopathy, renal failure, as well as rewarming shock. In order to avoid these complications the degree and duration of hypothermia has been shortened thereby limiting its effectiveness.

Generally, cooling of the brain has been accomplished through whole body cooling with use of a cooling blanket, immersing the patient in ice, or cooling the blood through a cardiopulmonary bypass machine. A few methods have been described regarding selective brain and spinal cord hypothermia. These involve cooling the arterial vessel or blood supply to the brain or external cooling helmets, each with its own significant limitations.

Several catheters have been developed to induce systemic hypothermia by inserting them into the bloodstream. More recently catheters have been developed that can be inserted into the arterial vessels to the brain to induce selective brain hypothermia. These catheters are limited in their size and finctionality by the small vessel lumen as well the inability to cool all the four major arterial vessels supplying blood to the brain and are unable to cool the spinal cord via this methodology. They also carry the risk of ischemic and thromboembolic stroke by either impairing the blood flow to the brain or dislodging clots that can develop in intra-arterial catheters.

External cooling helmets have limited effectiveness since the blood to the cooled scalp does not circulate into the brain and returns systemically which along with the thick skull dilutes the hypothermic effect to the brain.

Selective brain and spinal cord cooling with insertion of catheters into the ventricular, subdural or epidural space as described in U.S. Pat. No. 6,699,269 to Khanna is a novel concept. It also describes a catheter that expands with circulation of a coolant without direct contact of the coolant with the central nervous system. This avoids the side effects and complications seen from other methods of cooling. It also circumvents infection and fluid overload with exacerbation of brain swelling that can be potentially encountered with cooling systems involving circulating the cerebrospinal fluid. Implanted catheters are prone to the complications of obstruction and infection. In order to circumvent these complications, strategies have been developed which include use of systemic or local antibiotics and impregnating catheter walls with antibiotics and metals. While these methodologies have shown some effectiveness, the risk of complications still remains high. Several catheters capable of delivering ultrasonic or laser energy for blood clot hemolysis have been described. There is no prior art for a catheter with the capability of selective brain hypothermia induction and ultrasound or laser energy use to maintain catheter patency. The use of ultrasound and/or laser energy along with anti-clotting and antimicrobial agents is also a novel concept and prevents catheter obstruction from blood clots and debris as well as infection.

SUMMARY OF THE INVENTION

The invention provides a method and apparatus for performing selective hypothermia to the brain and/or the spinal cord for injury protection without the need for systemic cooling.

For selective brain cooling, in one embodiment of the present invention, a flexible catheter is inserted into the cerebral lateral ventricle to cool the cerebrospinal fluid and henceforth brain. The catheter has three lumens with a distal heat conductive element which also has holes to allow for drainage of cerebrospinal fluid. Two lumens are connected at the tip of the catheter and allow for circulation of a coolant. The third lumen has holes at the distal end that allows for drainage of cerebrospinal fluid as well as intracranial pressure monitoring similar to a ventriculostomy. In another embodiment of this catheter, ultrasonic or laser energy is delivered either through the catheter wall or lumen. Catheters placed in the brain or ventricles carry a high risk of occlusion from blood as well as infection. Ultrasonic or laser energy provides clot lyses and maintains catheter patency. Impregnation of the catheter wall with anticoagulant/antithrombotic and antimicrobial agents which are slowly released also reduces the risk of catheter obstruction and infection.

For selective spinal cord cooling, in another embodiment of the catheter described above, a catheter with a longer distal heat conductive element is inserted into the lumbar subdural or epidural space to allow for cooling around the spinal cord. This catheter may or may not have a lumen for drainage of cerebrospinal fluid.

In another embodiment of the catheter, a balloon located at the distal end of the catheter expands when the coolant fluid is circulated. The expansion also opens the third lumen distal holes further to maintain patency.

The catheters are designed to allow an inert coolant to circulate in the lumens without direct exposure to the brain or spinal cord and thereby altering the brain or spinal cord temperature. This allows for selective cooling of the brain and spinal cord for treatment of injury from trauma, ischemia, hypoxia and/or cerebral swelling.

BRIEF DESCRIPTION OF THE DRAWINGS

FIG. 25 is a cross-sectional side view of another embodiment of the catheter.

FIG. 26 is a cross-sectional view of the catheter taken along line A in FIG. 25.

FIG. 27 is a cross-sectional view of the catheter taken along line B in FIG. 25.

FIG. 28 is a cross-sectional side view of another embodiment of the catheter.

FIG. 29 is a cross-sectional side view of another embodiment of the catheter.

FIG. 30 is a cross-sectional side view of another embodiment of the catheter.

FIG. 31 is a cross-sectional side view of another embodiment of the catheter.

DETAILED DESCRIPTION OF THE PREFERRED EMBODIMENTS

Figure 1:
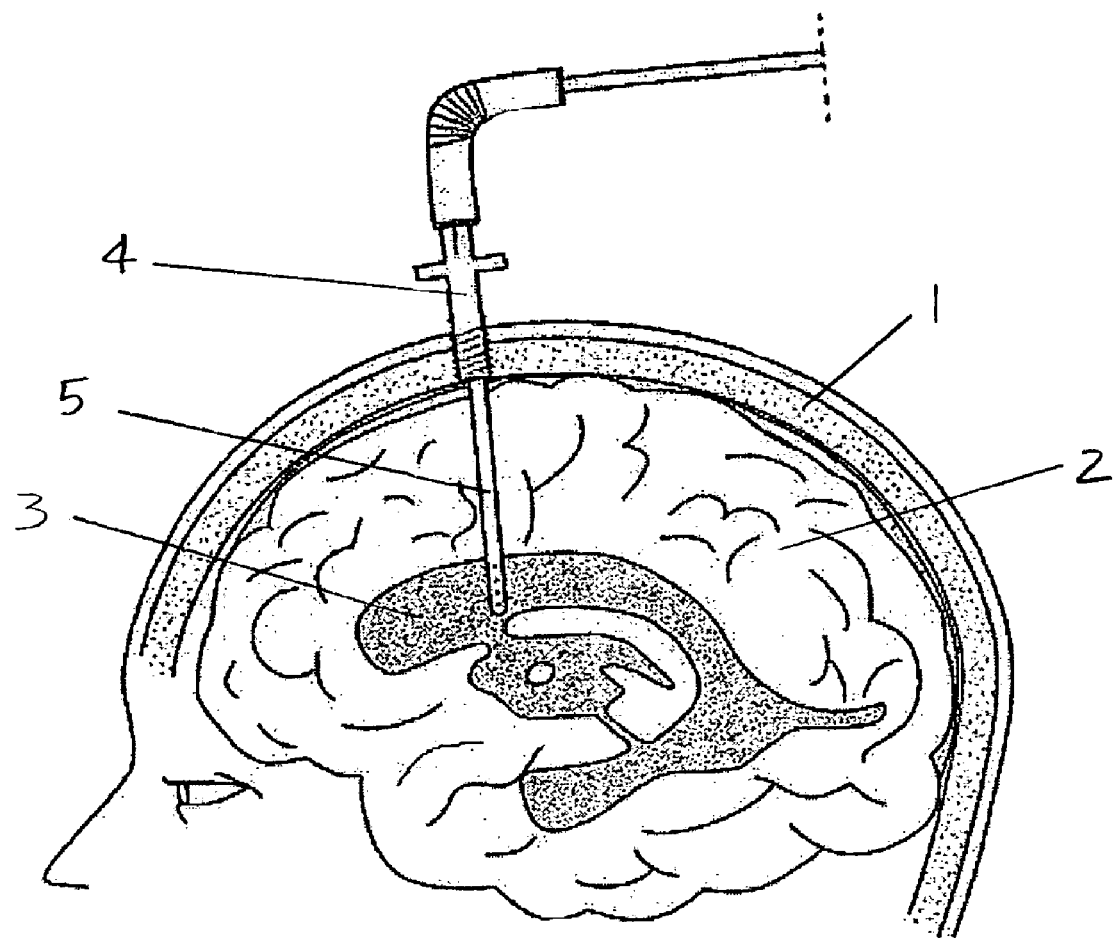
FIG. 1 is a schematic view of the catheter in the brain ventricle.

In one method of selective brain and/or spinal cooling, a catheter as shown in FIG. 1, can be placed into the ventricle of the brain or the subdural space of the spine. This allows for cooling of the cerebrospinal fluid and hence the brain and/or spinal cord selectively. These catheters can be placed in the lateral ventricles using the standard landmarks or can be precisely placed with stereotactic guidance or use of an endoscope. The bolt 4 secures the catheter 5 to the skull 1. The catheter 5 is placed into the cerebrospinal fluid in the ventricle 3.

Figure 2:
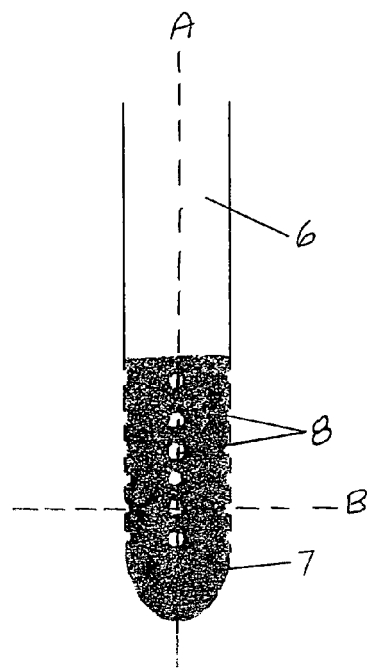
FIG. 2 is a top view of one embodiment of the catheter.

As illustrated in FIG. 2, the catheter has a proximal portion 6 and a distal heat transfer element 7. The distal heat transfer element 7 has several circumferential holes 8 that allow drainage of cerebrospinal fluid as well as monitoring of intracranial pressure.

Figure 3:
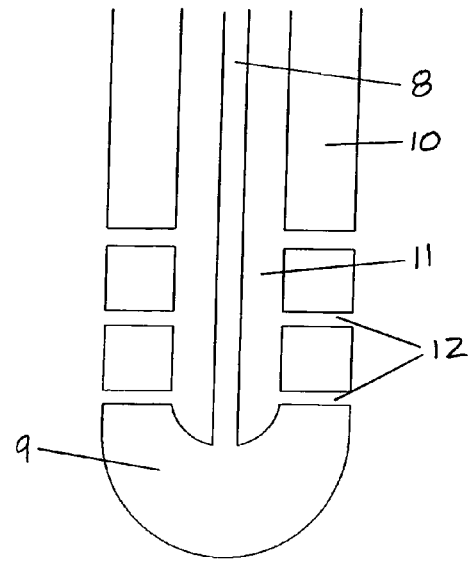
FIG. 3 is a cross-sectional longitudinal view of the catheter taken along line A in FIG. 2.
Figure 4:
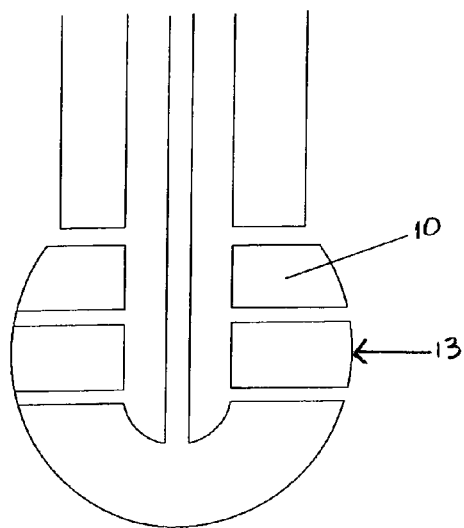
FIG. 4 is a cross-sectional longitudinal view of the catheter taken along line A in FIG. 2.
Figure 5:
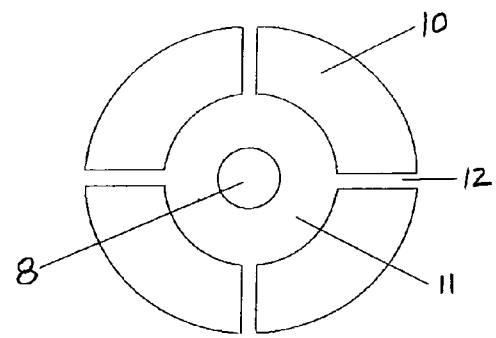
FIG. 5 is a cross-sectional transverse view of the catheter taken along line B in FIG. 2.

In one embodiment of the cooling catheter as shown in FIGS. 3-5, the heat exchange fluid or compressed refrigerant enters through the central lumen 8 into the distal end of the heat transfer element 9. The coolant or the gaseous refrigerant returns through the outer lumen 10. The circulation of the coolant through the catheter cools the distal heat transfer element, thereby allowing the cerebrospinal fluid surrounding the catheter to be cooled. Lumen 11 provides for drainage of the cerebrospinal fluid through the holes 12. The heat transfer element 13 is also capable of expanding like a balloon when fluid under pressure is circulated through lumen 10.

Figure 6:
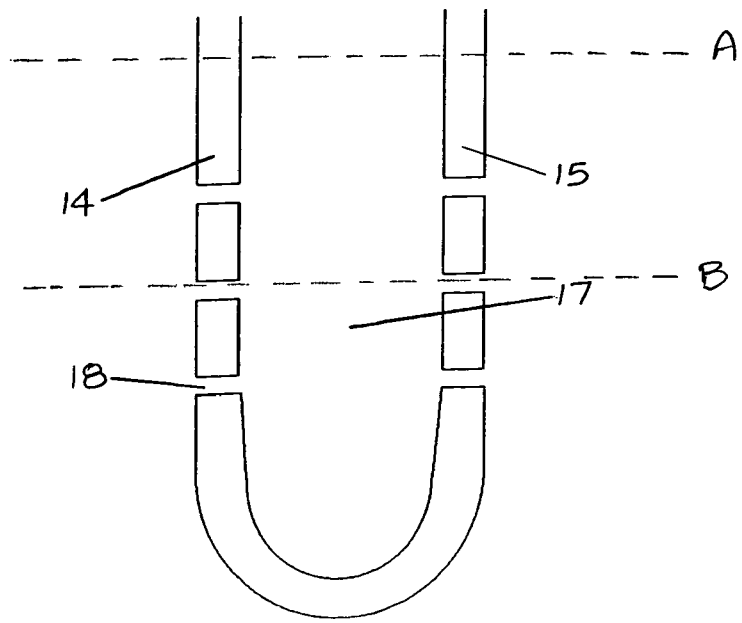
FIG. 6 is a cross-sectional side view of another embodiment of the catheter.
Figure 7:
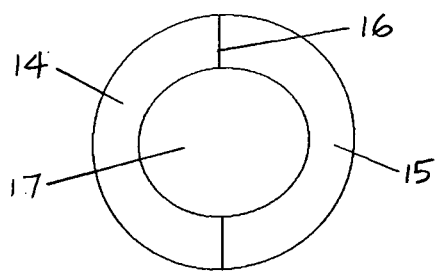
FIG. 7 is a cross-sectional view of the catheter taken along line A in FIG. 6.
Figure 8:
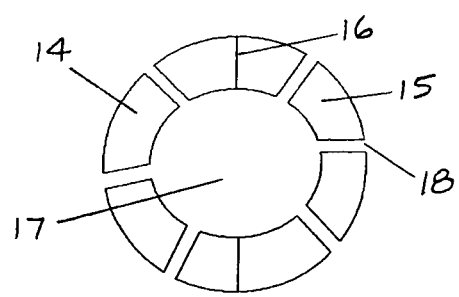
FIG. 8 is a cross-sectional view of the catheter taken along line B in FIG. 6.

In another embodiment of the cooling catheter as shown in FIGS. 6-8, a coolant enters through lumen 14 into the distal end of the catheter and returns through lumen 15. The lumens 14 and 15 are separated by a membrane 16. The central lumen 17 allows drainage of the cerebrospinal fluid through the holes 18.

Figure 9:
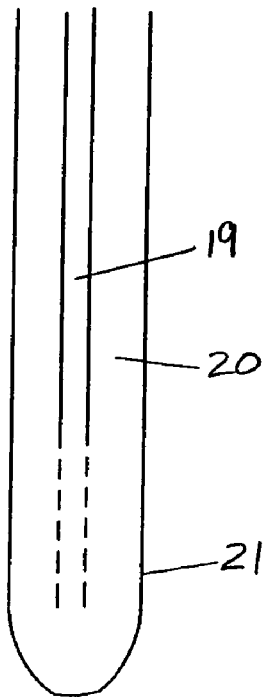
FIG. 9 is a cross-sectional side view of another embodiment of the catheter.
Figure 10:
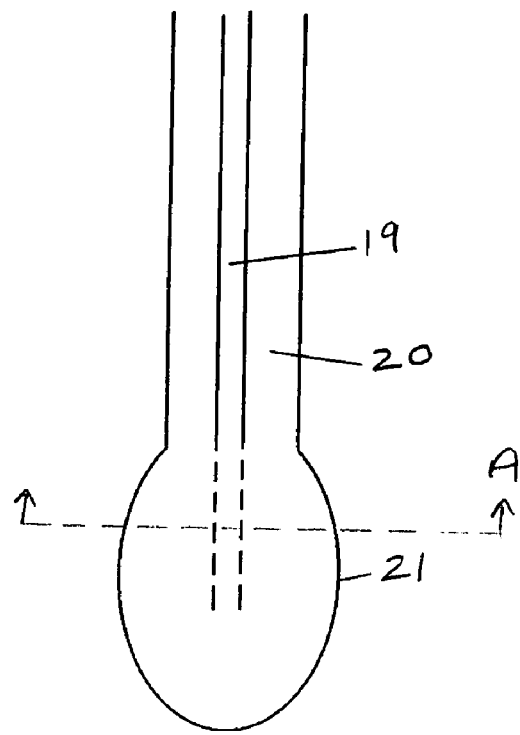
FIG. 10 is another cross-sectional side view of the catheter in FIG. 9.
Figure 11:
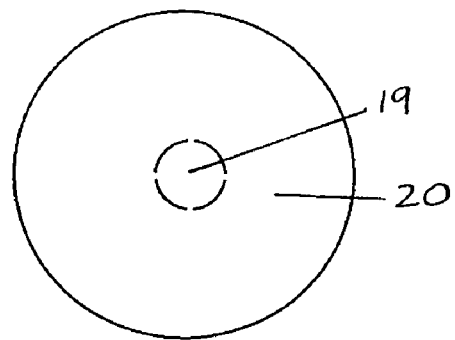
FIG. 11 is a cross-sectional view of the catheter taken along line A in FIG. 10.

In another embodiment of the cooling catheter as shown in FIGS. 9-11, a coolant enters into the distal end of the catheter through lumen 19 and returns through lumen 20. The distal catheter end 21 is capable of expanding like a balloon to increase the surface area of heat transfer when the coolant is circulated under pressure.

Figure 12:
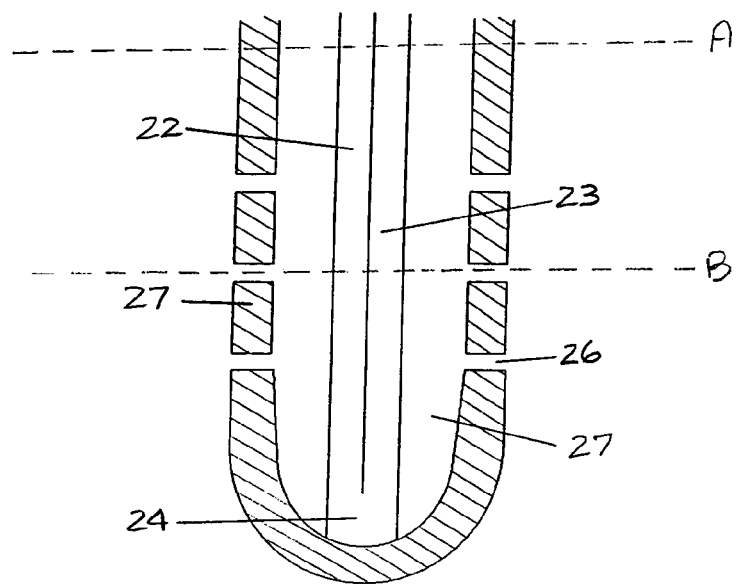
FIG. 12 is a cross-sectional side view of another embodiment of the catheter.
Figure 13:
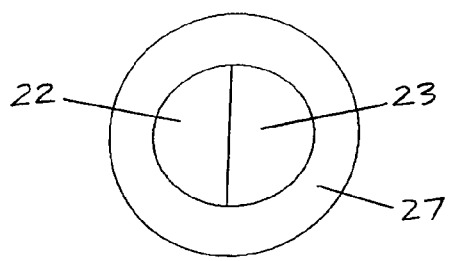
FIG. 13 is a cross-sectional view of the catheter taken along line A in FIG. 12.
Figure 14:
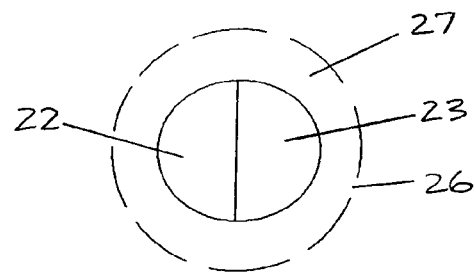
FIG. 14 is a cross-sectional view of the catheter taken along line B in FIG. 12.

In another embodiment of the cooling catheter as shown in FIGS. 12-14, a coolant is circulated through central lumens 22 and 23 in the catheter which communicate at the distal end 24. Lumen 25 allows drainage of the cerebrospinal fluid through the holes 26 in the catheter wall 27.

Figure 15:
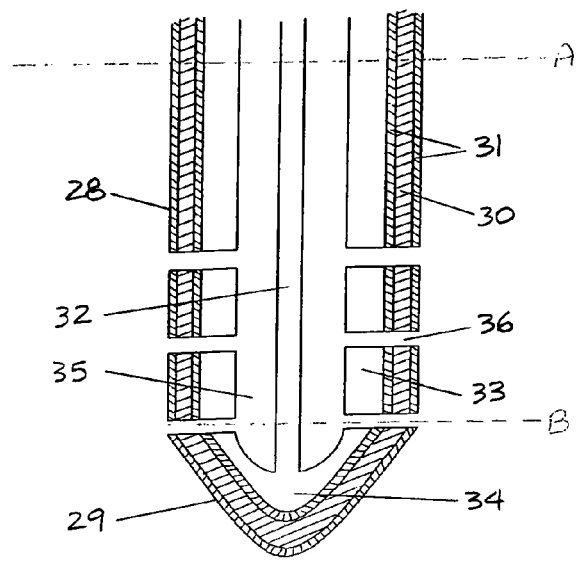
FIG. 15 is a cross-sectional side view of another embodiment of the catheter.
Figure 16:
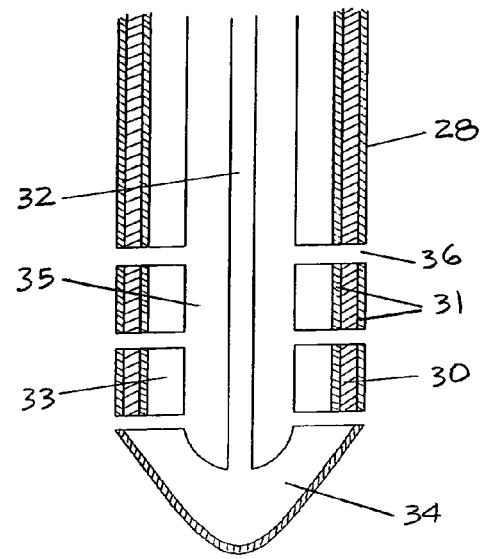
FIG. 16 is a cross-sectional side view of another embodiment of the catheter.
Figure 17:
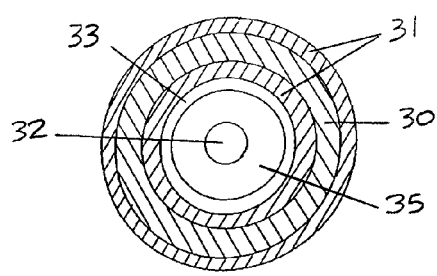
FIG. 17 is a cross-sectional view of the catheter taken along line A in FIG. 15.
Figure 18:
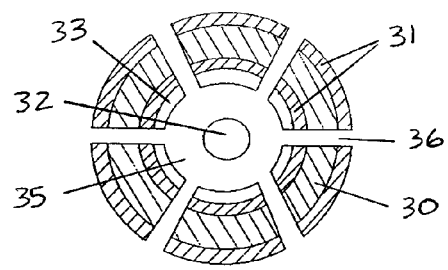
FIG. 18 is a cross-sectional view of the catheter taken along line B in FIG. 15.

FIGS. 15-18 illustrate an ultrasonic catheter system also capable of cooling. The distal catheter wall 28 as seen in FIG. 16 or the wall 28 and tip 29 as seen in FIG. 15 contain the ultrasound transducer with a piezoelectric crystal 30 surrounded by electrodes 31. The catheter contains three lumens. The central lumen 32 communicates with the outer lumen 33 at the distal end 34 and circulates a coolant to dissipate the heat generated from the ultrasound and also cool the brain. The intermediate lumen 35 contains ports 36 at the distal end that communicate with the external environment. When the catheter lumen becomes obstructed from a blood clot or debris, the ultrasonic energy dissolves the clot which can be further facilitated if needed by infusing a hemolytic or thrombolytic or antiplatelet agent through lumen 35 and then draining the liquefied blood through the same lumen. Since this lumen communicates with the brain, it can also be used to monitor the intracranial pressure.

Figure 19:
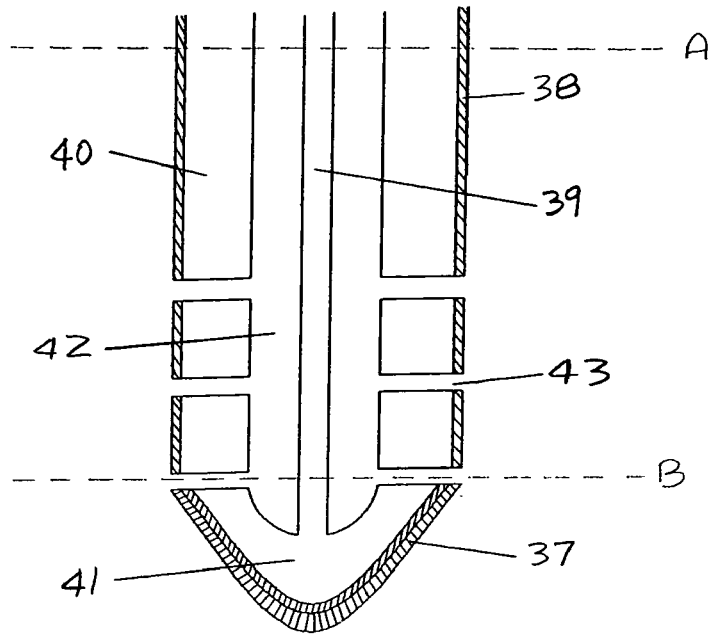
FIG. 19 is a cross-sectional side view of another embodiment of the catheter.
Figure 20:
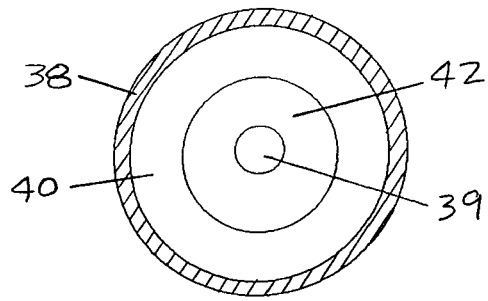
FIG. 20 is a cross-sectional view of the catheter taken along line A in FIG. 19.
Figure 21:
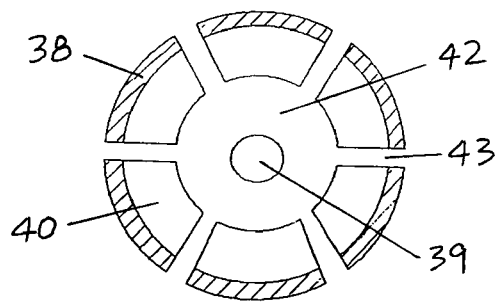
FIG. 21 is a cross-sectional view of the catheter taken along line B in FIG. 19.

FIGS. 19-21 illustrate an ultrasonic catheter with the transducer at the distal tip 37. The ultrasound transducer electrodes 38 are embedded in the catheter wall. The catheter contains three lumens. The central lumen 39 communicates with the outer lumen 40 at the distal end 41 and circulates a coolant. The intermediate lumen 42 contains ports 43 at the distal portion of the catheter.

Figure 22:
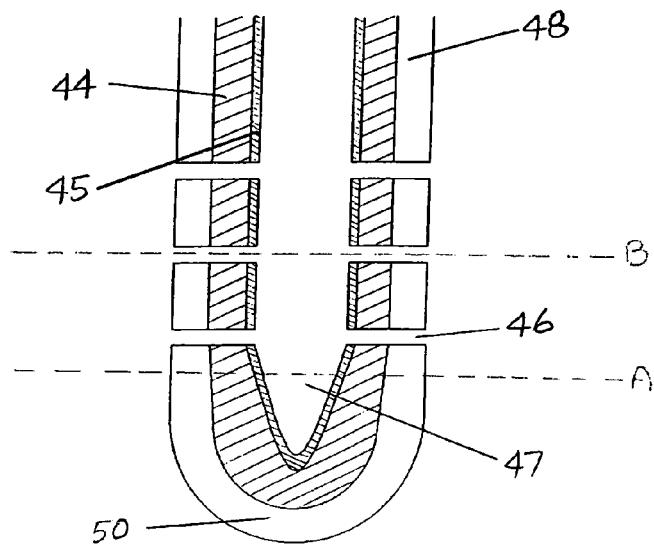
FIG. 22 is a cross-sectional side view of another embodiment of the catheter.
Figure 23:
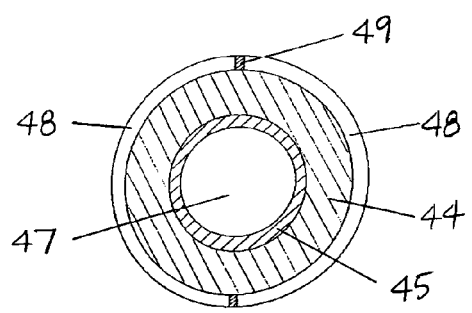
FIG. 23 is a cross-sectional view of the catheter taken along line A in FIG. 22.
Figure 24:
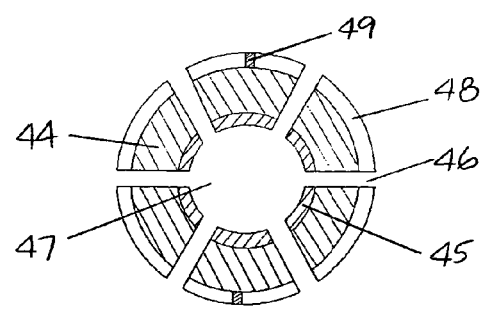
FIG. 24 is a cross-sectional view of the catheter taken along line B in FIG. 23.
Figure 32:
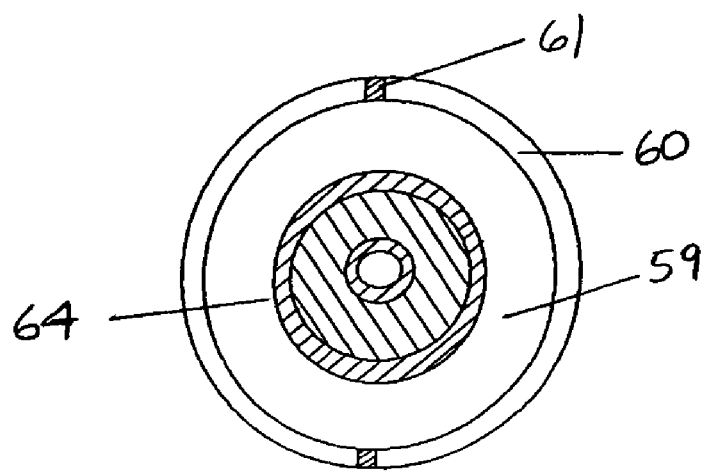
FIG. 32 is a cross-sectional view of the catheter taken along line A in FIG. 28.
Figure 33:
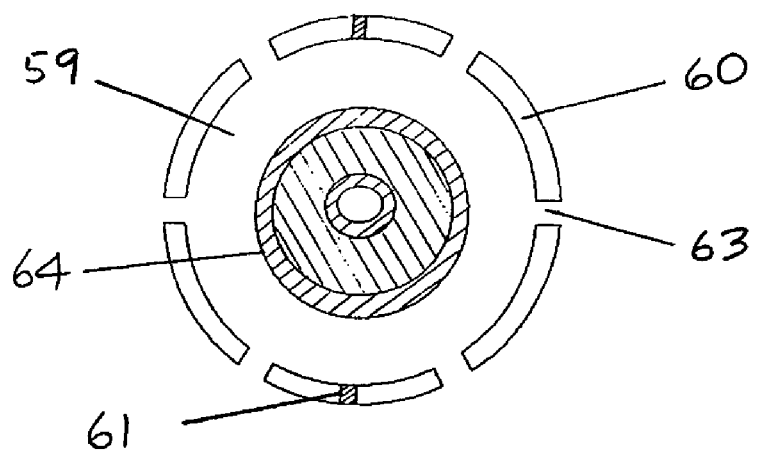
FIG. 33 is a cross-sectional view of the catheter taken along line B in FIG. 28.

FIGS. 22-24 illustrate another embodiment of the ultrasonic cooling catheter. The catheter contains two lumens separated by an ultrasound transducer. The inner lumen 47 communicates with the outside environment through ports 46. The outer lumen 48 is split into two halves by the wall 49 which communicate at the distal end 50 and allow for a coolant to circulate. The ultrasound transducer is embedded between the two lumens and contains the piezoelectric element 44 and the electrode 45.

In another embodiment of the ultrasonic cooling catheter as illustrated in FIGS. 25-27, the outer lumen 51 contains ports 52 to drain fluid or blood. The inner lumen 53 contains a wall 54 and split's the lumen into two halves which communicate at the distal end 55 to allow circulation of a coolant. The ultrasound transducer embedded between these lumens contains the piezoelectric element 56 with the electrodes 57 along with an amplifier 58.

In another embodiment of the ultrasonic cooling catheter as illustrated in FIGS. 28-33, the catheters contain two lumens 59 and 60. The outer lumen 60 is split into two halves by the wall 61 which communicate at the distal end 62 and allow for a coolant to circulate. The inner lumen 59 communicates with the outside environment through ports 63. The lumen 59 is also capable of incorporating an ultrasound transducer or conductor 64 which is removable. This catheter would be more suited for dissolving clots or obstructions in the catheter through ultrasonic energy and maintain catheter patency with periodic use. FIG. 30 illustrates a similar catheter with an anchor 65 at the distal end for the removable ultrasound transducer or conductor 64. This anchor can also serve as an amplifier for the ultrasound energy. FIG. 31 illustrates the catheter with the ultrasound transducer removed.

Figure 34:
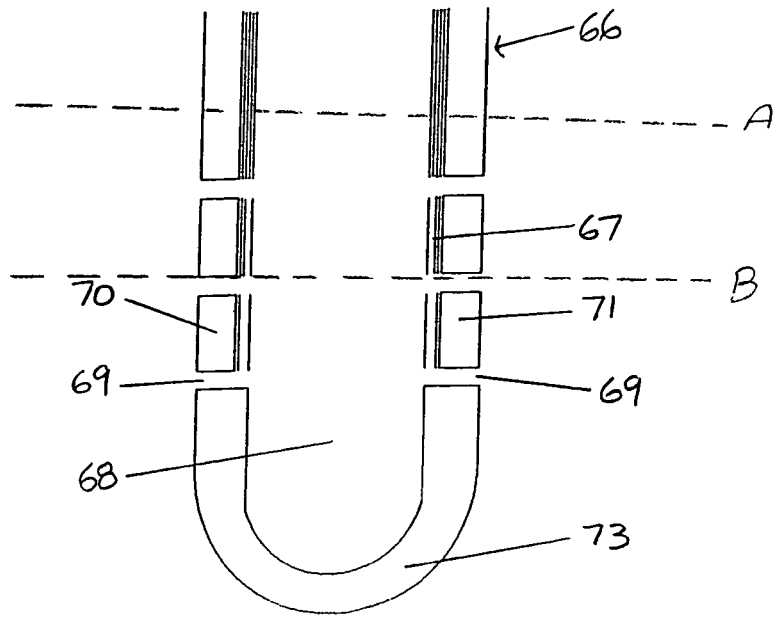
FIG. 34 is a cross-sectional side view of another embodiment of the catheter.
Figure 35:
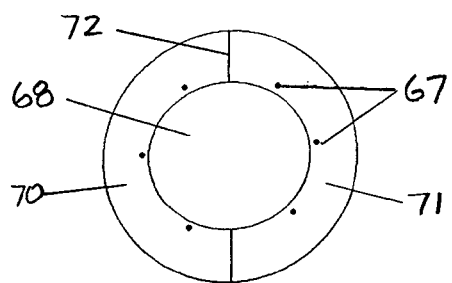
FIG. 35 is a cross-sectional view of the catheter taken along line A in FIG. 34.
Figure 36:
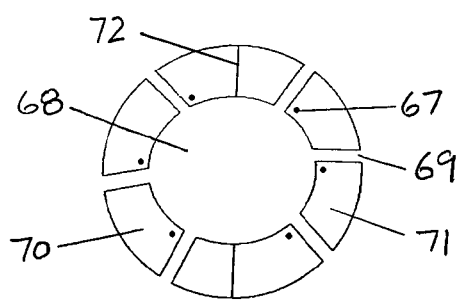
FIG. 36 is a cross-sectional view of the catheter taken along line B in FIG. 34.

FIGS. 34-36 illustrate a laser catheter system also capable of cooling. The distal catheter wall 66 contains optical fibers 67. The central catheter lumen 68 communicates with the outer environment through ports 69. The catheter wall contains a lumens 70 and 71 divided into two halves by a wall 72 which communicate at the distal end 73. A coolant is circulated through the lumens 70 and 71 to dissipate the heat generated from the laser and also cool the brain. The laser energy dissolves the clot obstructing the catheter lumen 68 which can be further facilitated if needed by infusing a hemolytic or thrombolytic or antiplatelet agent through lumen 68 and then draining the liquefied blood through the same lumen. Since this lumen communicates with the brain, it can also be used to monitor the intracranial pressure.

Figure 37:
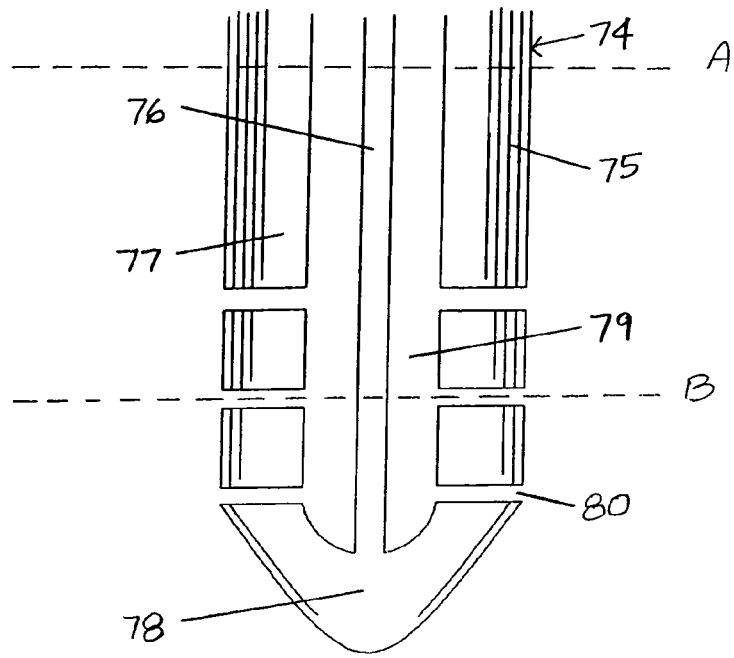
FIG. 37 is a cross-sectional side view of another embodiment of the catheter.
Figure 38:
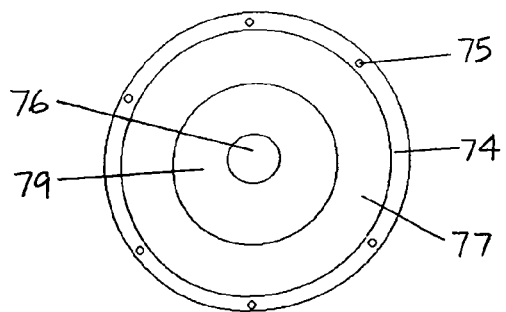
FIG. 38 is a cross-sectional view of the catheter taken along line A in FIG. 37.
Figure 39:
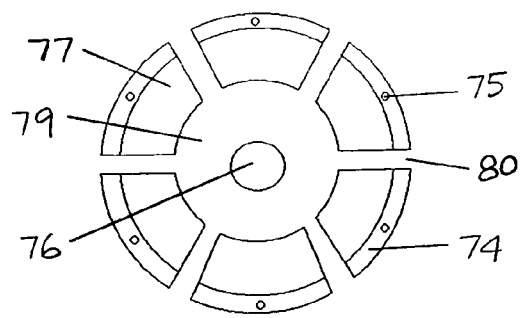
FIG. 39 is a cross-sectional view of the catheter taken along line B in FIG. 37.

In another embodiment as illustrated in FIGS. 37-39, the catheter wall 74 contains optical fibers 75 that are coupled to a laser source and transmit energy to dissolve clotted blood in the brain. The catheter contains three lumens. The central lumen 76 communicates with the outer lumen 77 at the distal end 78 and circulate a coolant to cool the cerebrospinal fluid and/or brain and also dissipate the heat generated from the laser energy. The middle lumen 79 contains ports 80 at the distal end that allow drainage of blood and/or cerebrospinal fluid. The lumen 79 can also be used to administer medications or agents to facilitate blood dissolution and/or neuroprotection.

Figure 40:
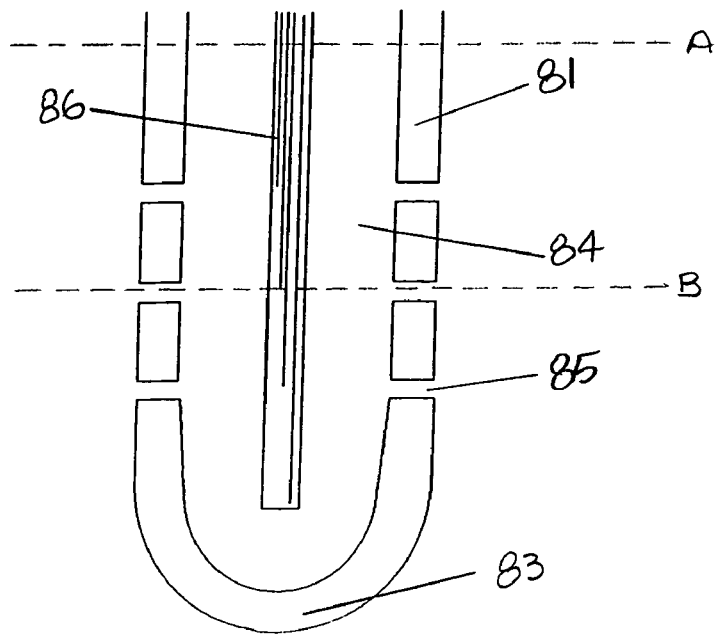
FIG. 40 is a cross-sectional side view of another embodiment of the catheter.
Figure 41:
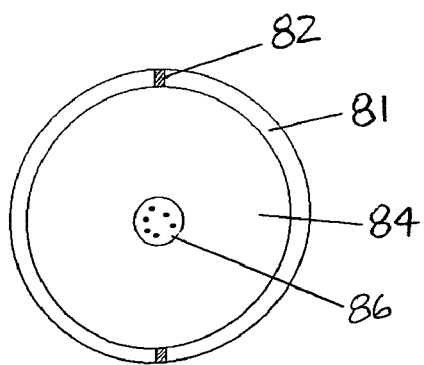
FIG. 41 is a cross-sectional view of the catheter taken along line A in FIG. 40.
Figure 42:
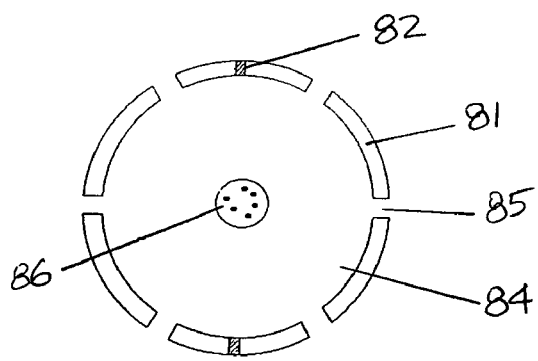
FIG. 42 is a cross-sectional view of the catheter taken along line B in FIG. 40.

In another embodiment as shown in FIGS. 40-42, the catheter contains two lumens. The outer lumen 81 is divided into two halves by a wall 82 and communicate at the distal end 83. A coolant is circulated through lumen 81 to cool the brain or spinal cord. The central lumen 84 contains ports 85 at the distal end. Removable optical fibers 86 can be inserted into the lumen 84 as needed to dissolve clotted blood.

Figure 43:
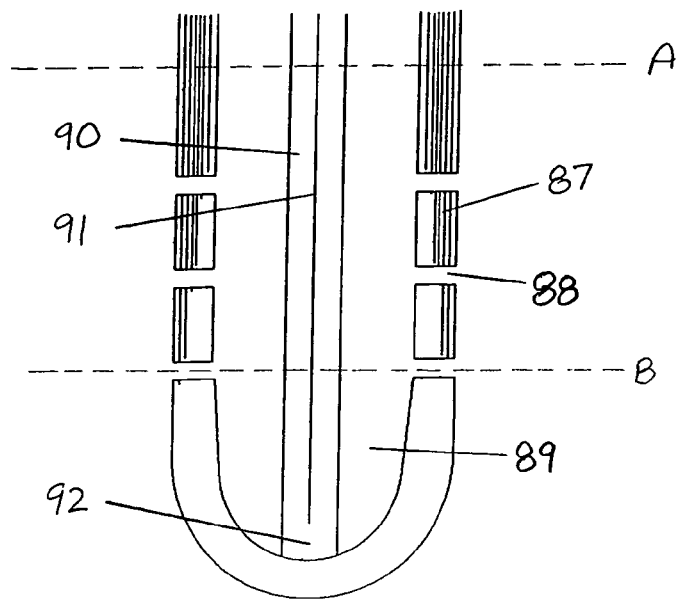
FIG. 43 is a cross-sectional side view of another embodiment of the catheter.
Figure 44:
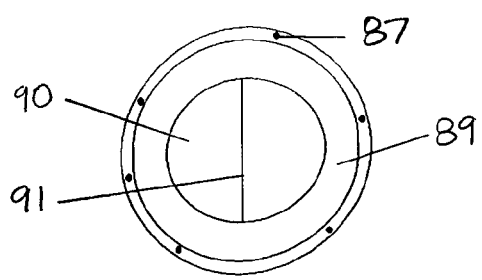
FIG. 44 is a cross-sectional view of the catheter taken along line A in FIG. 43.
Figure 45:
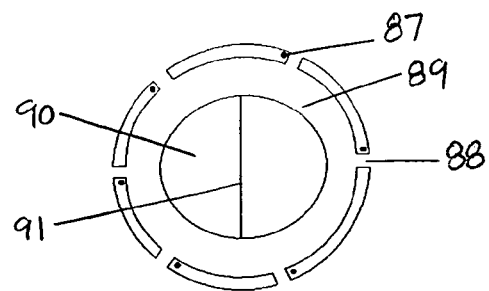
FIG. 45 is a cross-sectional view of the catheter taken along line B in FIG. 43.

FIGS. 43-45 illustrate a catheter with optical fibers in the wall 87. The wall also contains ports 88 that communicate with the lumen 89. The central lumen 90 is divided into two halves by a wall 91 that communicate at the distal end 92 and allows for circulation of a coolant.

Figure 46:
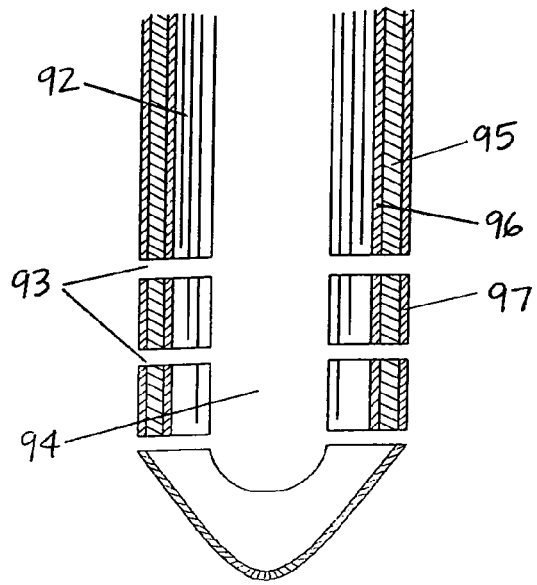
FIG. 46 is a cross-sectional side view of another embodiment of the catheter.
Figure 47:
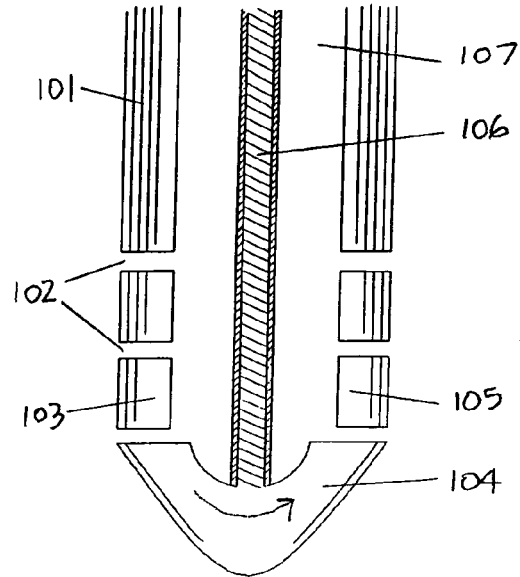
FIG. 47 is a cross-sectional side view of another embodiment of the catheter.
Figure 48:
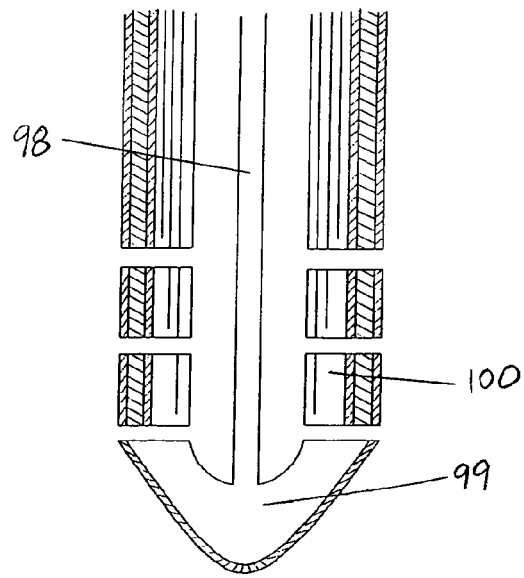
FIG. 48 is a cross-sectional side view of another embodiment of the catheter.

A catheter system providing for central nervous system cooling while also incorporating the ultrasound and laser energy to dissolve and drain blood clots from the central nervous system and maintain catheter patency is illustrated in FIGS. 46-48. As shown in FIG. 46, the catheter wall contains optical fibers 92 along with ports 93 that communicate with the lumen 94. The ultrasound transducer contains a piezoelectric element 95 surrounded by electrodes 96 and 97. In another embodiment as shown in FIG. 48, the catheter also contains a central lumen 98 that communicates at the distal end 99 with lumen 100 and allows for a coolant to circulate to cool the central nervous system and also dissipate heat generated from the lasers and ultrasound. In another embodiment as shown in FIG. 47, the catheter wall contains optical fibers 101 along with ports 102 that communicate with the lumen 107. The ultrasound transducer 106 is surrounded by the lumen 107. The catheter also contains lumens 103 and 105 that communicate at the distal end 104 and circulate a coolant.

Figure 49:
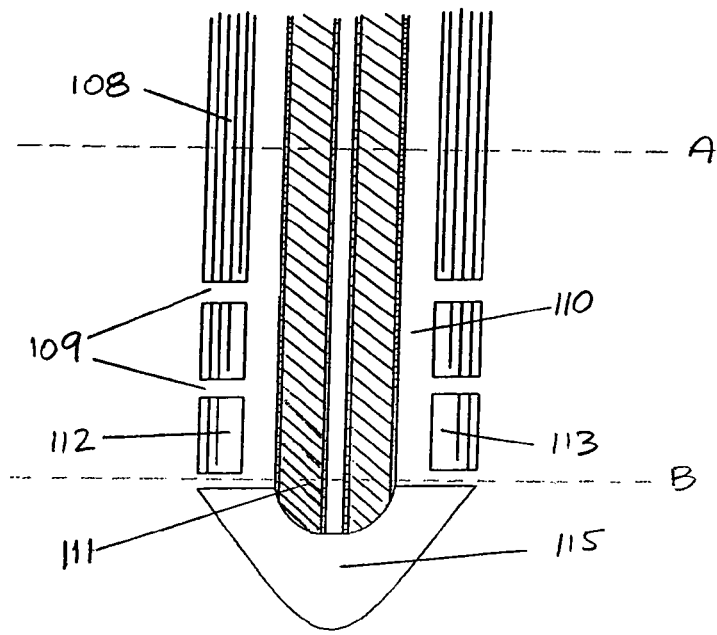
FIG. 49 is a cross-sectional side view of another embodiment of the catheter.
Figure 50:
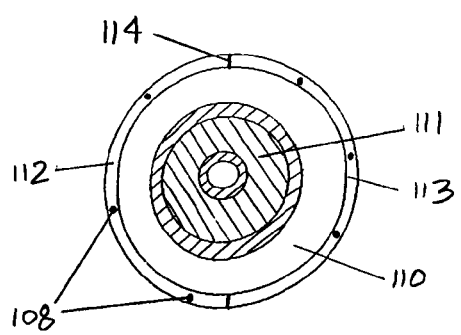
FIG. 50 is a cross-sectional view of the catheter taken along line A in FIG. 49.
Figure 51:
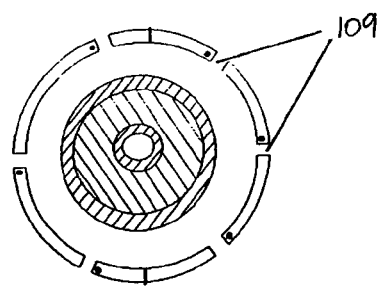
FIG. 51 is a cross-sectional view of the catheter taken along line B in FIG. 49.

FIGS. 49-51, illustrate a catheter with optical fibers 108 in the outer wall that also contains ports 109 at the distal end that connect the outer environment to the lumen 110. The lumen 110 also contains the ultrasound transducer 111. The catheter wall also contains lumens 112 and 113 which are split by a wall 114 that allows communication between the two lumens at the distal end 115. A coolant is circulated through lumens 112 and 113 to cool the central nervous system and also dissipate heat generated from the lasers and ultrasound.

Figure 52:
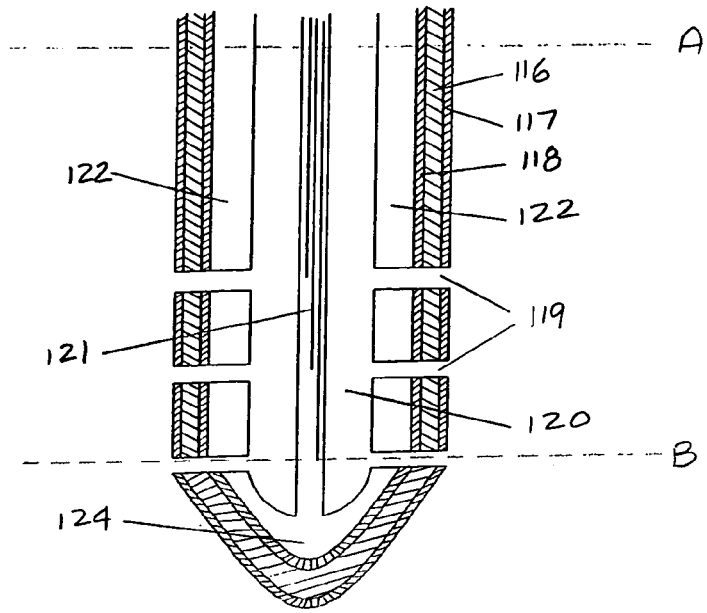
FIG. 52 is a cross-sectional side view of another embodiment of the catheter.
Figure 53:
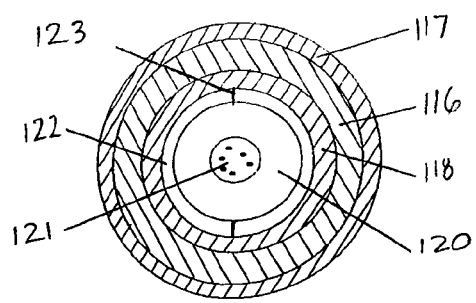
FIG. 53 is a cross-sectional view of the catheter taken along line A in FIG. 52.
Figure 54:
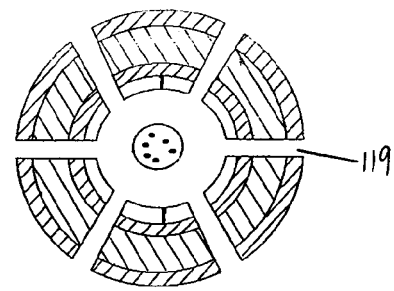
FIG. 54 is a cross-sectional view of the catheter taken along line B in FIG. 52.
Figure 55:
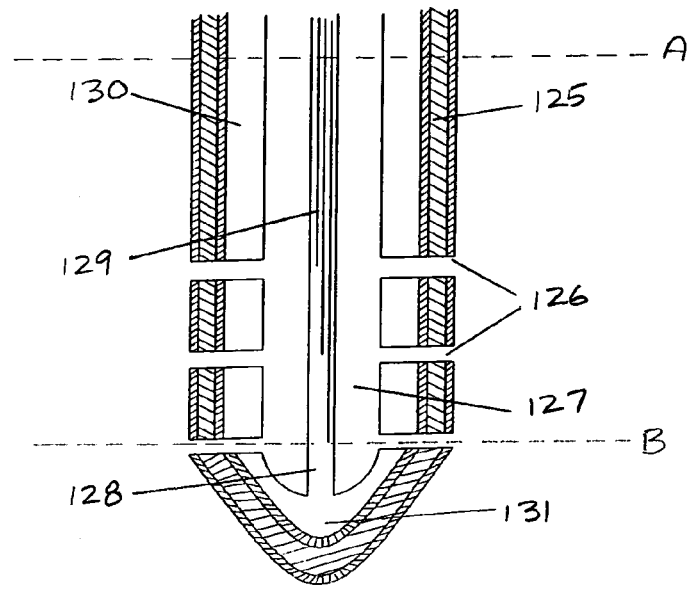
FIG. 55 is a cross- sectional side view of another embodiment of the catheter.
Figure 56:
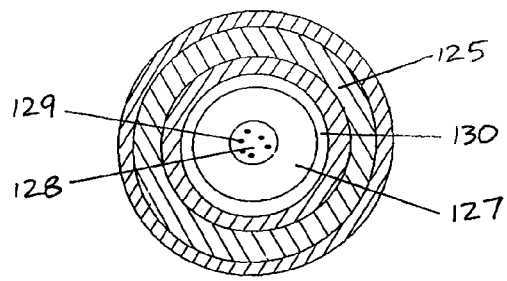
FIG. 56 is a cross-sectional view of the catheter taken along line A in FIG. 55.
Figure 57:
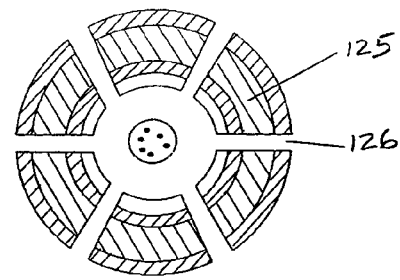
FIG. 57 is a cross-sectional view of the catheter taken along line B in FIG. 55.
Figure 58:
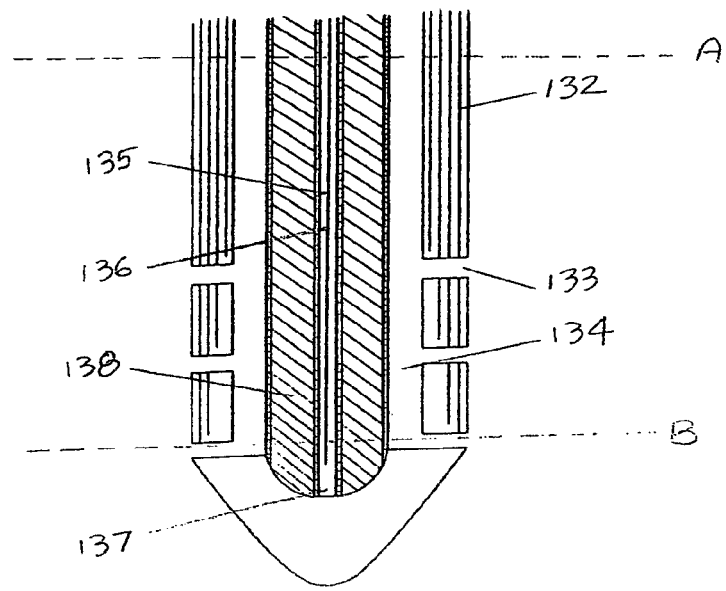
FIG. 58 is a cross-sectional side view of another embodiment of the catheter.
Figure 59:
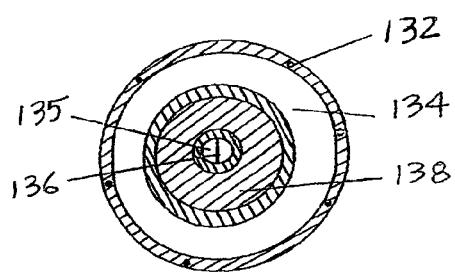
FIG. 59 is a cross-sectional view of the catheter taken along line A in FIG. 58.
Figure 60:
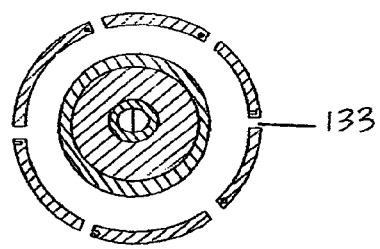
FIG. 60 is a cross-sectional view of the catheter taken along line B in FIG. 58.

In another embodiment as shown in FIGS. 52-54, the catheter wall contains the ultrasound transducer with the piezoelectric element 116 surrounded by the electrodes 117 and 118. The distal end of the catheter wall also contains ports 119 that communicate with the lumen 120. The central lumen 120 contains the laser optical fibers 121. The lumen 122 is split by a wall 123 that allows communication at the distal end 124 and circulates a coolant. In another embodiment as illustrated in FIGS. 55-57, the catheter wall contains the ultrasound transducer 125 with ports 126 that connect with the lumen 127. The lumen 127 contains another lumen 128 which harbors the optical fibers 129 and also circulates a coolant which connects with the outer lumen 130 at the distal end 131. In another embodiment illustrated in FIGS. 58-60, the catheter contains laser optical fibers 132 embedded in the wall and ports 133 communicating with the lumen 134. The central lumen 135 is split in two halves by a wall 136 that connect at the distal end 137 and circulate a coolant. The ultrasound transducer 138 surrounds the central cooling lumen 135.

Figure 61:
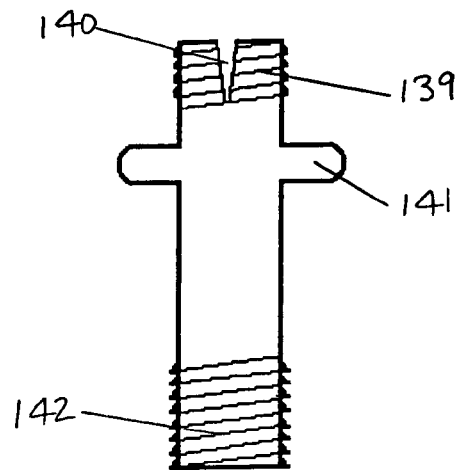
FIG. 61 is a top view of the bolt.
Figure 62:
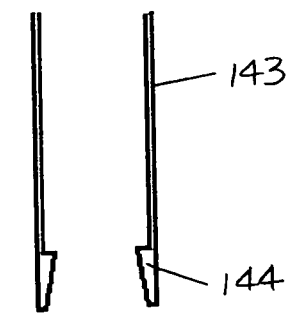
FIG. 62 is a cross-sectional view of the outer bolt sheath.
Figure 63:
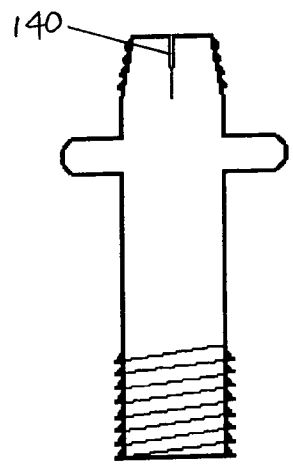
FIG. 63 is another top view of the bolt.
Figure 64:
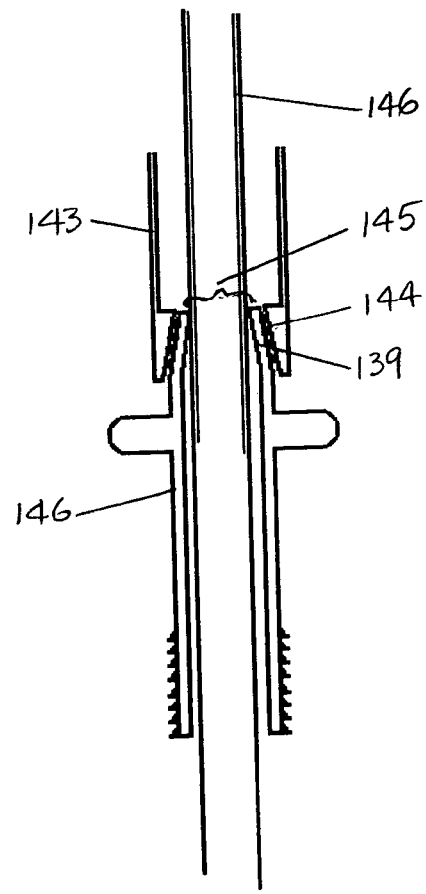
FIG. 64 is a cross-sectional view of the sheath connected to the bolt.

FIGS. 61-64 illustrate a bolt used to secure the catheter to the skull. The T-shaped bolt as seen in FIG. 61 comprises of threads 142 which secure to a hole drilled in the skull and threads 139 that secure the outer sheath 143. The bolt also contains handles 141 and slits 140. The outer sheath 143 also contains threads 144 as shown in FIG. 62. As illustrated in FIG. 63 the slits 140 are capable of closing when the outer sheath is secured and tightened to the bolt. FIG. 63 illustrates the bolt 146 with the outer sheath 143 secured. The sheath threads 144 are secured to the bolt threads 139 and when tightened lead to the closure of the slits 140 which compresses the bolt wall to narrow the bolt opening 145 and secures the catheter 146 to the bolt.

While the methodology described herein is specific for central nervous system cooling and prevention of catheter obstruction and infection, its use is not limited to this particular pathology. These catheters can also be used to treat various other central nervous system pathologies. For instance, ultrasonic and/or laser energy directly transmitted into a brain blood clot or tumor with the catheter system allows for clot hemolysis and drainage as well as tumefaction and dissolution of the tumor cells which can then be drained directly. Similarly heat or cold variation through the catheter can also facilitate the tumefaction process along with a direct delivery of a chemotherapeutic agent.

What is claimed is:

1. A method of cooling the central nervous system wherein a heat exchange catheter is inserted into the central nervous system and a coolant is circulated through the catheter to transfer heat from the surrounding area to the coolant wherein the catheter comprises; i) an elongate flexible catheter with a proximal and distal end, ii) a lumen which is split into two halves by a longitudinal wall which communicates at the distal end, iii) an expandable thermal conductor located at the distal end of the catheter allowing transfer of heat between the said heat exchanger and its surroundings; iv) circulating a coolant with temperature below the body temperature through the lumen, thereby transferring heat from the central nervous system to the coolant.

2. The method of claim 1 wherein, said expandable thermal conductor comprises a balloon.

3. The method of claim 1 wherein, the said central nervous system consists of one or more of the following locations: cerebrospinal fluid, subarachnoid, subdural, epidural, ventricle, cerebral, spinal.

4. The method of claim 1 wherein, the said catheter is impregnated with antimicrobial and/or anti-clotting agents comprising of one or more of the following: antibiotics, antifungal, iodine, metals, polymeric material, antibodies, anticoagulant, anti-platelet, thrombolytic, chlorhexidine gluconate, anti-inflammatory.

5. The method of claim 1 wherein, the said catheter also delivers ultrasonic and/or laser energy.

6. The method of claim 1, further comprising the act of securing a catheter to the skull with: a T-shaped bolt with a lumen for the catheter and threads at the proximal and distal ends; the distal end of the bolt secures to the skull through a hole drilled into the skull; the proximal end of the bolt secures an outer sleeve; the proximal bolt end also comprising of slits that compress and nanow the lumen and secure the catheter once the outer sleeve is tightened.

7. A method of cooling the central nervous system wherein a heat exchange catheter device is inserted into the central nervous system, a coolant is circulated through the catheter to transfer heat from the surrounding area to the coolant; a portion of the catheter capable of expanding; the catheter also comprising another lumen to drain fluid.

8. The method of claim 7 wherein, the heat exchange catheter device comprises; i) an elongate flexible catheter with a proximal and distal end, ii) two lumens which communicate at the distal catheter end and circulate the coolant, thereby transferring heat from the central nervous system to the coolant, iii) a heat exchanger balloon located at the distal end of the catheter which expands when the coolant is circulated, iv) a third lumen with several holes at the distal end that communicate with the external catheter environment and allow for fluid drainage and pressure monitoring.

9. The method of claim 7 wherein, the heat exchange catheter device comprises; i) an elongate flexible catheter with a proximal and distal end, ii) an inner and an outer lumen, iii) the inner lumen of the catheter communicates with the external catheter environment through several holes at the distal end, iv) the outer lumen is split in the center into two halves by a longitudinal wall which connect at the distal catheter end; v) circulating the coolant through the outer lumen, thereby transferring heat from the central nervous system to the coolant.

10. The method of claim 7 wherein, the heat exchange catheter device comprises; i) an elongate flexible catheter with a proximal and distal end, ii) an inner and an outer lumen, iii) the inner lumen of the catheter communicates with the external catheter environment through several holes at the distal end, iv) the outer lumen is split in the center into two halves by a longitudinal wall which connect at the distal catheter end; v) a thermal conductor located at the distal end of the catheter allowing transfer of heat between the said heat exchange catheter and its surroundings; vi) circulating the coolant through the outer lumen, thereby transferring heat from the central nervous system to the coolant.

11. The method of claim 7 wherein, the said central nervous system consists of one or more of the following locations:
   cerebrospinal fluid, subarachnoid, subdural, epidural, ventricle, cerebral, spinal.

12. The method of claim 7 wherein, the said catheter also delivers ultrasonic and/or laser energy.

13. The method of claim 7 wherein, the said catheter is impregnated with antimicrobial and/or anti-clotting agents comprising of one or more of the following: antibiotics, antifungal, iodine, metals, polymeric material, antibodies, anticoagulant, anti-platelet, thrombolytic, chlorhexidine gluconate, anti-inflammatory.

14. A method of cooling the central nervous system wherein a heat exchange catheter is inserted into the central nervous system; a coolant is circulated through the catheter to transfer heat from the surrounding area to the coolant; the catheter also comprising another lumen to drain fluid and a delivery means to maintain catheter lumen patency.

15. The method of claim 14 wherein, the said delivery means to maintain catheter patency is through ultrasound energy delivered through the catheter to dissolve blood clots.

16. The method of claim of claim 15, wherein said ultrasound energy delivery being through one or more of the following: i) an ultrasound transducer embedded in the catheter wall, ii) an ultrasound transducer in the lumen of the catheter which may be removable, iii) ultrasound energy generated outside the catheter and delivered to the catheter through a conductor, iv) an ultrasound transducer in the catheter with a distal amplifier, v) an ultrasound conductor in the catheter with a distal amplifier.

17. The method of claim 14 wherein, the said delivery means to maintain catheter patency is through a combination of ultrasound and laser energy delivered through the catheter to dissolve blood clots and debris.

18. The method of claim 17, wherein said ultrasound and laser energy being delivered through one or more of the following: i) optical fibers in the catheter wall and ultrasound transducer in the lumen, ii) optical fibers and ultrasound transducer embedded in the catheter wall, iii) ultrasound transducer in the catheter wall and optical fibers in the lumen.

19. The method of claim 14 wherein, the said means to maintain catheter patency is through a combination of ultrasound and laser energy delivered through the catheter to dissolve blood clots and debris and a suction device to facilitate drainage through the said another lumen to drain fluid.

20. The method of claim 14 wherein, the said catheter wall is impregnated with antimicrobial and/or anti-clotting agents comprising of one or more of the following: antibiotics, antifungal, iodine, metals, polymeric material, antibodies, anticoagulant, anti-platelet, thrombolytic, chlorhexidine gluconate, anti-inflammatory.

21. The method of claim 14 wherein, the said means to maintain catheter patency is through ultrasound and/or laser energy delivered through the catheter to dissolve blood clots and debris; blood clot dissolution further facilitated by
   one or more of the following agents infused through the said lumen to drain fluid: i) thrombolytics like streptokinase, urokinase, prourokinase, ancrod, tissue plasminogen activators (alteplase, anistreplase, tenecteplase, reteplase, duteplase), ii) hemolytic agents, iii) antiplatelet agents like aspirin, ticlopidine, clopidogrel, dipyridamole, iv) anticoagulants like heparin and coumadin.

22. The method of claim 14, further comprising the act of securing a catheter to the skull with: a T-shaped bolt with a lumen for the catheter and threads at the proximal and distal ends; the distal end of the bolt secures to the skull through a hole drilled into the skull; the proximal end of the bolt secures an outer sleeve; the proximal bolt end also comprising of slits that compress and narrow the lumen and secure the catheter once the outer sleeve is tightened.

23. The method of claim 14 wherein, the said means to maintain catheter patency is through photonic or electromagnetic energy delivered through a catheter laser system to dissolve blood clots and debris in the catheter lumen and ports.

24. The method of claim 23, wherein said photonic or electromagnetic energy delivery being through one or more of the following; i) optical fibers in the catheter wall coupled to a laser source at the proximal end, ii) optical fibers in the catheter lumen coupled to a laser source which may be removable.

25. The method of claim 7, further comprising the act of securing a catheter to the skull with: a T-shaped bolt with a lumen for the catheter and threads at the proximal and distal ends; the distal end of the bolt secures to the skull through a hole drilled into the skull; the proximal end of the bolt secures an outer sleeve; the proximal bolt end also comprising of slits that compress and narrow the lumen and secure the catheter once the outer sleeve is tightened.

* * * * *